United States Patent [19]

Keshavaraja et al.

[11] Patent Number: 5,723,679
[45] Date of Patent: Mar. 3, 1998

[54] PROCESS FOR THE PREPARATION OF METHYL ETHYL KETONE FROM AN SECONDARY BUTYL ALCOHOL USING AN IMPROVED COPPER SILICA CATALYST

[75] Inventors: Alive Keshavaraja, Mangalore; James Violet Samuel; Arumugamangalam Venkataraman Ramaswamy, both of Pune, all of India

[73] Assignee: Council of Scientific & Industrial Research, New Delhi, India

[21] Appl. No.: 649,024

[22] Filed: May 16, 1996

[51] Int. Cl.[6] .................................................. C07C 45/00
[52] U.S. Cl. ........................ 568/406; 568/403; 502/345
[58] Field of Search ........................... 568/403, 406; 502/345

[56] References Cited

U.S. PATENT DOCUMENTS 4,453,015  6/1984  Slaugh et al. .......................... 568/406

OTHER PUBLICATIONS

Kawamoto et al; "Bull. Soc.Chim(Japan)";vol. 41; #4; pp. 932–936, 1968.

*Primary Examiner*—Paul J. Killos
*Assistant Examiner*—Sreeni Padmanabhan
*Attorney, Agent, or Firm*—Michael D. Bednarek; Kilpatrick Stockton LLP

[57] ABSTRACT

A process for the production of methyl ethyl ketone by means of oxidative dehydrogenation of secondary butyl alcohol using an amorphous copper-silica catalyst prepared by a sol-gel route, in which an alkoxide or other suitable salt or complex of copper is reacted with an alkoxide of silicon in the absence of base, but in the presence of water or an alcohol; the resultant product is dried and calcined.

9 Claims, No Drawings

5,723,679

PROCESS FOR THE PREPARATION OF METHYL ETHYL KETONE FROM SECONDARY BUTYL ALCOHOL USING AN IMPROVED COPPER SILICA CATALYST

This invention relates to an improved process for the preparation of methyl ethyl ketone (MEK) using a supported copper dehydrogenation catalyst. More specifically, the process developed in the present invention relates to the production of methyl ethyl ketone by the dehydrogenation of secondary butyl alcohol (SBA) using an improved copper catalyst supported on silica prepared by a novel soligel method.

Methyl ethyl ketone is an important industrial chemical and has been widely used as a solvent in the vinyl resins and synthetic rubber industries. The dehydrogenation of secondary butyl alcohol over various metal oxide catalysts at 250°–400° C. results in the formation of varying amount of unconverted alcohol, water and MEK. MEK is produced commercially from SBA which undergoes catalytic dehydrogenation over a mixture of active copper supported on kieselguhr or pumice. High activity, selectivity and stability make the system one of the industrial catalysts available for alcohol dehydrogenation.

The active copper catalysts are known in the prior art for a long time for various dehydrogenation reactions, for example, Indian patent 161835 (1984) describes the convesrsion of ethyl alcohol to acetaldehyde, while the other (Indian Patent No 167222/1988) disclosed copper oxide hydrogenation catalyst for the conversion of crotonaldehyde to n-butanol. A recent Indian Patent Application No 303/DEL/93 describes the conversion of secondary butyl alcohol to methyl ethyl ketone using a cppper catalyst supported on silica prepared by co-precipitation technique. Although various methods are known in the prior art to prepare an active catalyst, there is one or the other limitation with respect to either the activity or selectivity or the life time of the catalyst. It is very important to control and optimize the preparation procedure so that catalyst with high surface area, high metal area and good dispersion of the active metal on the surface of the support can be obtained. All these criteria of the good dehydrogenation catalyst are fulfilled when a novel method of preparation of the supported copper catalyst by sol gel method is adopted.

Accordingly, the object of the present invention is to provide an improved process for the preparation of methyl ethyl ketone by oxidation/dehydogenation of secondary butyl alcohol using an improved supported copper catalyst prepared by a novel sol-gel procedure the details of which are described in the co-pending patent application. The preparation process comprises of reacting an alkoxide of silicon with an alkoxide or any other convenient salt of copper in the presence of water or any other non aqueous solvent preferrably aliphatic alcohols which dissolves the copper salt or copper alkoxide at a temperature in the range of 20° to 90° C., drying the resultant gel at a temperature in the range of 100° to 150° C. and further calcining the dried powder at a temperature ranging from 250° to 500° C. The alkoxide of silicon which may be advantageously used include ethoxide, isopropoxide or butoxide. The salts of copper which may be used include chlorides, acetates, nitrates or any other salt or complexes of copper. A significant feature in the preparation of the catalyst for the process of the present invention is that precipitating agents such as ammonium hydroxide or any other hydroxide is not used and thus there is no precipitation of any salt of the component used in the present oxide. The catalyst thus prepared is amorphous in nature and has improved textural, physical, chemical and mechanical properties with high surface area, low bulk density and high dispersion of the copper.

According to one embodiment of the present invention, the catalyst is reduced under hydrogen flow insitu in the fixed bed reactor, the concentration of hydrogen being varied from 10% to 100% and the rest is either nitrogen or argon. The production of methyl ethyl ketone comprises of passing a feed consisting of secondary butyl alcohol in its vapor form over fixed bed of an improved copper silica catalyst prepared by sol-gel method at LHSV in the range of 1 to 20 per hour at temperature in the range of 210°–350° C. at a pressure of 1–5 atms. Pure methyl ethyl ketone may be recovered by distillation.

More specifically, in the said process, a liquid feed of secondary butyl alcohol is passed at a liquid hourly space velocity (LHSV) of 4 to 12 per hour in to the fixed bed reactor kept at temperature range of 200° C. to 300° C. and the product was analysed for the methyl ethyl ketone and other byproducts and the unreacted secondary butyl alcohol. Generally, greater than 99% selectivity to MEK is achieved while the conversion of secondary butyl alcohol was greater than 96% as compared to the hitherto known commercial catalyst with 90% activity and selectivity to MEK equal to 95%.

The present invention is further described with reference to the following examples which are for illustrative purpose only and should not be construed to limit the scope of the present invention.

EXAMPLE 1

Preparation of the Amorphous Copper Silica Catalyst 100 g of tetraethyl orthosilicate and 20 mole % of copper acetate dissolved in ethylalcohol were reacted together at 50° C. for 48 hours in presence of water as hydrolysing agent. The blue coloured gel thus obtained was dried at 100° C. for 24 hour and subsequently calcined at 300° C. for 12 hour and treated under the flow of hydrogen (20%) for 8 hour at a temperature of 300° C. The resultant catalyst was amorphous as evidenced by X-ray diffraction pattern and the surface area of the sample was found to be 550 m$^2$/g.

EXAMPLE 2

1.5 g (−10 to 20 #) of the catalyst (surface area 575 m$^2$/g and the apparent bulk density 0.55 g/ml) prepared by the process described in the example 1 is loaded in a 1 m long and 1.5 cm internal diameter reactor provided with an axial thermocouple. The catalyst was reduced in 10% H$_2$N$_2$ mixture in a flow at 30 ml/min, raising the catalyst bed temperature slowly to 270° C. in 10 hours and holding at that temperature for about 5 hours. The concentration and the flow rate of SBA was adjusted to 10 ml per hour, i.e LHSV of 5 h$^{-1}$. The reactor was heated up to 240° C. and the preheated feed of secondary butyl alcohol in its vaporised form was introduced over the prereduced catalyst bed. The pressure at outlet was 1 bar. The products, both liquid and gaseous were analysed by GC equipped with carbowax column (2 m long) and kept at 110° C. (isothermal) with FI detector using N$_2$ as the carrier gas. In addition, the by-products such as olefins along with the unconverted SBA were also quantitatively estimated. The SBA converted was 97 mole % and the selectvity to MEK was 99.9%.

EXAMPLE 3

15 g of CuO/SiO$_2$ catalyst prepared by the procedure cited at example 1 made in the form of 4 mm×5mm prereduced cylindrical pellets were loaded in the reactor 1 m long and 20 cm internal diameter and heated up to 240° C. for testing with 16 ml/h feed rate i.e. LHSV of 8 h$^{-1}$. The MEK conversion was 94% and the selectivity to methyl ethyl ketone was 99.9%.

EXAMPLE 4

This example essentially gives the effect of reaction temperature on the catalytic activity performance given in Table 1). The rest of the run conditions are identical to those as described in Example 2.

TABLE 1

| Temperature (°C.) | Conversion (mole %) | % Selectivity to MEK |
|---|---|---|
| 200 | 63.0 | 99.99 |
| 220 | 75 | 99.99 |
| 240 | 94.2 | 99.99 |
| 260 | 95.0 | 99.98 |
| 280 | 95.6 | 99.85 |
| 300 | 97.0 | 99.80 |

EXAMPLE 5

This example gives the effect of space velocity on the catalytic performance. The rest of the reaction condition is similar to that described in the example 2

| LHSV (h$^{-1}$) | Conversion (mole %) | % Selectivity to MEK |
|---|---|---|
| 1.25 | 97.0 | 99.90 |
| 2.50 | 96.5 | 99.90 |
| 5.00 | 94.20 | 99.99 |
| 7.50 | 90.0 | 99.95 |
| 10.0 | 80.8 | 99.98 |
| 12.5 | 75.0 | 99.97 |
| 15.0 | 73.0 | 99.98 |

We claim:

1. An improved process for the preparation of methyl ethyl ketone from secondary butyl alcohol which comprises contacting the alcohol at a temperature ranging from about 210° C. to 350° C. with a catalyst consisting essentially of copper embedded on an amorphous silica matrix, wherein the copper content ranges from about 1 to 50 mole % with respect to silica, the catalyst being prepared by a sol-gel route from alkoxides or salts of silicon and copper.

2. The process of claim 1, wherein the catalyst has a surface area ranging from about 400 to 700 m$^2$/g and a pore radius between about 5 and 40 Å.

3. The process of claim 1, wherein the catalyst is prepared by reacting an alkoxide or other salt or complex of copper with an alkoxide of silicon in the absence of any base, but in presence of water or an alcohol, at a temperature in the range of about 20° to 90° C., drying the resultant solid at about 100°–150 ° C., and further calcining the dry solid in an oxidizing atmosphere at a temperature ranging from about 200° to about 500° C.

4. The process according to claim 3, wherein subsequent to calcining said catalyst is reduced in situ in the reactor in a flow of a hydrogen-nitrogen mixture, wherein the H$_2$ concentration varies from about 10 to 100% and at a temperature up to about 280° C.

5. The process according to claim 3, wherein the alkoxide of silicon is tetraethyl orthosilicate and the alkoxide or other salt or complex of copper is at least one species selected from the group consisting of copper nitrate, copper acetate, copper chloride, copper alkoxide, and copper acetyl acetonate.

6. The process according to claim 1, wherein the CuO:SiO$_2$ mole ratio of the catalyst varies from 1:1 to 1:10.

7. The process according to claim 1 wherein the LHSV of secondary butyl alcohol is varied between 1 to 20 h$^{-1}$.

8. The process according to claim 1, wherein dehydrogenation is carried out in a fixed bed in the presence of a nitrogen flow at a pressure ranging from 1 to 5 atmospheres.

9. The process according to claim 1, wherein dehydrogenation is carried out in a fixed bed in the absence of a nitrogen flow.

* * * * *